US008821614B1

(12) United States Patent  (10) Patent No.: US 8,821,614 B1
Albenze et al.  (45) Date of Patent: Sep. 2, 2014

(54) CONSTANT PRESSURE HIGH THROUGHPUT MEMBRANE PERMEATION TESTING SYSTEM

(71) Applicants: Erik J. Albenze, Bethel Park, PA (US); David P. Hopkinson, Morgantown, WV (US); David R. Luebke, Bethel Park, PA (US)

(72) Inventors: Erik J. Albenze, Bethel Park, PA (US); David P. Hopkinson, Morgantown, WV (US); David R. Luebke, Bethel Park, PA (US)

(73) Assignee: U.S. Department of Energy, Washington, DC (US)

( * ) Notice: Subject to any disclaimer, the term of this patent is extended or adjusted under 35 U.S.C. 154(b) by 231 days.

(21) Appl. No.: 13/629,733

(22) Filed: Sep. 28, 2012

(51) Int. Cl.
*B01D 46/46* (2006.01)

(52) U.S. Cl.
USPC ............. 95/12; 95/43; 96/4; 73/37; 73/38

(58) Field of Classification Search
USPC ............. 95/12, 43; 96/4; 73/37, 38
See application file for complete search history.

(56) References Cited

U.S. PATENT DOCUMENTS

| | | | | | |
|---|---|---|---|---|---|
| 3,590,634 | A | * | 7/1971 | Pasternak et al. | 374/54 |
| 3,604,246 | A | * | 9/1971 | Toren | 73/38 |
| 3,618,361 | A | * | 11/1971 | Stephens | 73/38 |
| 3,822,202 | A | * | 7/1974 | Hoehn | 95/55 |
| 3,926,561 | A | * | 12/1975 | Lucero | 436/178 |
| 4,464,927 | A | | 8/1984 | Reid | |
| 4,852,389 | A | * | 8/1989 | Mayer et al. | 73/38 |
| 4,934,182 | A | * | 6/1990 | Eggertsen et al. | 73/73 |
| 5,107,696 | A | * | 4/1992 | Mayer et al. | 73/38 |
| 5,265,463 | A | * | 11/1993 | Loebig | 73/38 |
| 5,390,539 | A | * | 2/1995 | Mayer | 73/38 |
| 5,837,888 | A | * | 11/1998 | Mayer et al. | 73/38 |
| 7,306,647 | B2 | * | 12/2007 | Miller et al. | 95/45 |
| 7,329,304 | B2 | * | 2/2008 | Bliss et al. | 95/12 |
| 7,818,996 | B2 | | 10/2010 | Gevers et al. | |
| 8,117,899 | B2 | * | 2/2012 | Piombini et al. | 73/38 |
| 8,388,742 | B2 | * | 3/2013 | Nunes | 96/4 |
| 8,673,067 | B2 | * | 3/2014 | Liu et al. | 96/5 |
| 2003/0005750 | A1 | * | 1/2003 | Deckman et al. | 73/38 |
| 2008/0028834 | A1 | * | 2/2008 | Gevers et al. | 73/38 |
| 2009/0320564 | A1 | * | 12/2009 | Piombini et al. | 73/38 |
| 2010/0313752 | A1 | * | 12/2010 | Powell et al. | 95/45 |
| 2011/0168023 | A1 | * | 7/2011 | Nunes | 96/4 |

OTHER PUBLICATIONS

Howard et al., "Hydrogen permeance of palladium-copper alloy membranes over a wide range of temperatures and pressures," Journal of Membrane Science 241 (2004) 207-218.

* cited by examiner

*Primary Examiner* — Jason M Greene
*Assistant Examiner* — Anthony Shumate
(74) *Attorney, Agent, or Firm* — James B. Potts; Brian J. Lally; John T. Lucas

(57) ABSTRACT

The disclosure relates to a membrane testing system for individual evaluation of a plurality of planar membranes subjected to a feed gas on one side and a sweep gas on a second side. The membrane testing system provides a pressurized flow of a feed and sweep gas to each membrane testing cell in a plurality of membrane testing cells while a stream of retentate gas from each membrane testing cell is ported by a retentate multiport valve for sampling or venting, and a stream of permeate gas from each membrane testing cell is ported by a permeate multiport valve for sampling or venting. Back pressure regulators and mass flow controllers act to maintain substantially equivalent gas pressures and flow rates on each side of the planar membrane throughout a sampling cycle. A digital controller may be utilized to position the retentate and permeate multiport valves cyclically, allowing for gas sampling of different membrane cells over an extended period of time.

20 Claims, 3 Drawing Sheets

CONSTANT PRESSURE HIGH THROUGHPUT MEMBRANE PERMEATION TESTING SYSTEM

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

The disclosure relates to an apparatus and method of testing the individual performance of a plurality of planar membranes subjected to a feed gas on one side and a sweep gas on a second side. Retentate and permeate streams are individually and cyclically withdrawn from the individual membrane testing cells for evaluation of the planar membrane restrained therein, based on the relative compositions of the feed gas and the permeate stream withdrawn.

BACKGROUND

Membrane technologies have shown tremendous potential for a variety of separations, and new applications are constantly appearing. These new applications require exploration of materials, operational conditions, and membrane synthesis procedures, and demand accurate and timely evaluation of membrane properties and performance. Many different membrane materials may need to be screened in order to determine the most appropriate membrane for a separation application, and the large variety of potential membranes and the numerous parameters which may be varied generates a laborious and time intensive testing process using typically available methods.

Two general methods for membrane material evaluation are the variable-pressure method and the variable-volume method. In the variable-pressure method, a gas permeates through a film into a closed constant-volume chamber that is pre-evacuated, and the pressure rise in the chamber is recorded as a function of time. In the variable-volume method, the chamber into which a gas permeates is allowed to expand against a low constant pressure, and the volume change of the chamber is recorded as a function of time. The methods are widely used for the determination of steady-state permeation rates for pure gases.

For membrane evaluation when a prospective feed gas is a gas mixture, continuous flow is generally utilized in both the supply chamber and receiving chamber of a permeate cell, in order to avoid the build-up of concentration gradients in the cell. In general, the permeation rate will be different for each gas species in a gas mixture and continuous flow on both the retentate and permeate sides of a membrane during testing acts to mitigate the concentration gradients.

There is a huge variety of potential membrane materials for gas separations involving mixed gases. Additionally, the testing is often required to be conducted under a varying range of conditions, since membrane performance is typically dependent on a variety of factors such as feed pressures, temperatures, pH, feed concentrations, and so on, generating a large number of candidate membranes. It would be advantageous to provide a system whereby the testing of multiple membranes under substantially identical conditions could occur, in order to more rapidly evaluate a large number of candidate membranes for a given gas separation application. It would be additionally advantageous if the system operated in a continuous flow manner on both the retentate and permeate sides of the membrane, in order to allow effective evaluation against various gas mixtures. It, would be further advantageous if the system were designed such that while sampling the permeate and retentate gases of a given membrane, the non-tested membranes remained subject to the substantially the same conditions on both the permeate and retentate sides throughout the sampling rotation, so that performance over extended periods of time could be adequately evaluated.

Provided here is a membrane testing system providing the capability to test a plurality of planar membranes subjected to a feed gas on one side and a sweep gas on a second side. The membrane testing system continuously provides a pressurized and continuous flow of the feed gas and the sweep gas to each membrane testing cell while retentate and permeate streams are continuously withdrawn. The retentate and permeate streams of the plurality of membrane testing cells are ported to either a mass flow controller or a backpressure regulator by multiport valves, acting to maintain substantially equivalent pressures and flow rates on each planar membrane throughout a sampling cycle. The system allows the testing of multiple membranes under substantially identical conditions for rapid evaluation of candidate membranes for given gas separation applications and various gas mixtures, and maintains substantially constant conditions on both the permeate and retentate sides of non-sampled membranes with continuous flow throughout a sampling rotation, allowing consistent evaluation over extended periods of time.

These and other objects, aspects, and advantages of the present disclosure will become better understood with reference to the accompanying description and claims.

SUMMARY

The membrane testing system disclosed provides a capability to test the individual performance of a plurality of planar membranes subjected to a feed gas on one side and a sweep gas on a second side. The membrane testing system provides a pressurized and substantially constant flow of the feed gas to each membrane testing cell in a plurality of membrane testing cells, and provides a pressurized and substantially constant flow of the sweep gas to each membrane testing cell in the plurality of membrane testing cells. During operation, within an individual membrane testing cell, a planar membrane is restrained by a membrane holder and separates the feed gas and the sweep gas. Additionally, retentate and permeate streams are withdrawn from the individual membrane testing cell for evaluation of the planar membrane restrained therein, based on the relative compositions of the feed gas stream and the permeate stream withdrawn.

A main feed line receives feed gas through a feed mass flow controller and pressurizes the feed volume of individual membrane testing cells with a feed gas. Concurrently, a retentate conduit in each individual membrane testing cell withdraws a stream of retentate gas from the feed volume. The stream of retentate gas from each membrane testing cell is sent to a retentate multiport valve, and the retentate multiport valve ports a single retentate stream to a retentate sampling line and ports the remainder of the retentate lines to a retentate vent line. A retentate back pressure regulator and retentate mass flow controller act to maintain substantially equivalent feed gas flow rates and pressures on each planar membrane throughout a sampling cycle. Additionally, each individual membrane testing cell is comprised of a sweep volume pressurized by a main sweep line receiving sweep gas through a sweep mass flow controller. Concurrently, a permeate conduit in each individual membrane testing cell withdraws a stream of permeate gas. A permeate multiport valve ports a single permeate stream to a permeate sampling line and ports the remainder of the permeate lines to a permeate vent line. A permeate back pressure regulator and permeate mass flow controller acts to maintain substantially equivalent sweep gas pressures on each planar membrane throughout the sampling cycle.

A digital controller may be utilized to position the retentate multiport valve and permeate multiport valve cyclically for periodic sampling of each individual membrane testing cell. The digital controller may cycle through all the membrane testing cells in the membrane testing system in this manner, so that the performance of all membranes retained in the membrane testing cells may be evaluated for the specific feed gas pressure, feed gas composition, sweep gas pressure, permeate gas composition, and other variables.

The novel process and principles of operation are further discussed in the following description.

DETAILED DESCRIPTION

Figure 1:
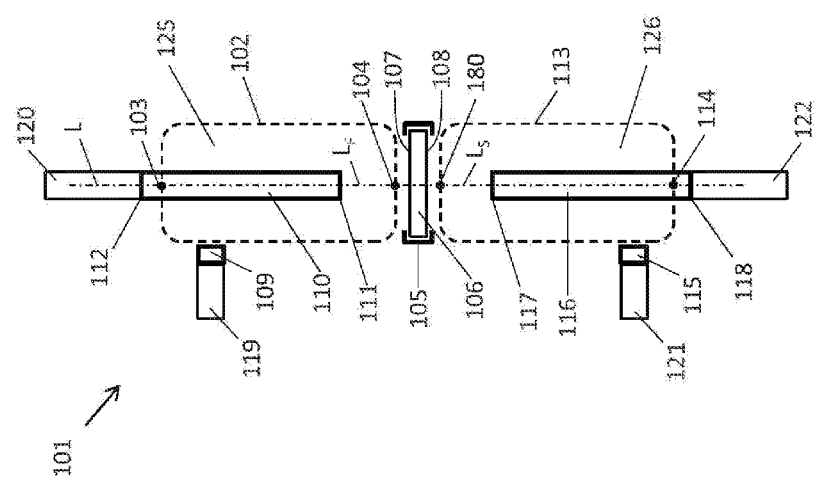
FIG. 1 illustrates an individual membrane testing cell

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a system and method for evaluating a plurality of planar membranes under constant pressure testing conditions.

The membrane testing system provides a capability to test the individual performance of a plurality of planar membranes subjected to a feed gas on one side and a sweep gas on a second side. The membrane testing system provides a pressurized and substantially constant flow of the feed gas to each membrane testing cell in a plurality of membrane testing cells, and provides a pressurized and substantially constant flow of the sweep gas to each membrane testing cell in the plurality of membrane testing cells. During operation, within an individual membrane testing cell, a planar membrane is restrained by a membrane holder and separates the feed gas and the sweep gas. Additionally, retentate and permeate streams are withdrawn from the individual membrane testing cell for evaluation of the planar membrane restrained therein, based on the relative compositions of the feed gas and the permeate stream withdrawn.

Each individual membrane testing cell is comprised of a feed volume in fluid communication with a main feed line having a plurality of main feed outlets. The main feed line receives feed gas through a feed mass flow controller, and each main feed outlet in the main feed line pressurizes the feed volume of an individual membrane testing cell with the feed gas. Concurrently, a retentate conduit in each individual membrane testing cell withdraws a stream of retentate gas from the feed volume. The stream of retentate gas from each membrane testing cell is sent to a retentate multiport valve, and the retentate multiport valve ports a single retentate stream to a retentate sampling line and ports the remainder of the retentate lines to a retentate vent line. The sampling line mass flow is controlled by a retentate mass flow controller, and the retentate flows from the remaining retentate lines are controlled by a retentate back pressure regulator. The retentate back pressure regulator and the retentate mass flow controller act to maintain substantially equivalent feed gas flow rates and pressures on each planar membrane throughout a sampling cycle, and the flow through system where feed gas is continuously applied and retentate continuously withdrawn greatly mitigates the generation of any concentration gradient within the individual membrane testing cells.

Additionally, each individual membrane testing cell is comprised of a sweep volume, which during operation is fluidly isolated from its feed volume by a planar membrane. The sweep volume is in fluid communication with a main sweep line having a plurality of main sweep outlets. The main sweep line receives sweep gas through a sweep mass flow controller, and each main sweep outlet in the main sweep line pressurizes the sweep volume of an individual membrane testing cell with the sweep gas. Concurrently, a permeate conduit in each individual membrane testing cell withdraws a stream of permeate gas from each membrane testing cell and sends it to a permeate multiport valve. The permeate multiport valve ports a single permeate stream to a permeate sampling line and ports the remainder of the permeate lines to a permeate vent line. The permeate sampling line mass flow is controlled by a permeate mass flow controller, and the permeate flows from the remaining permeate lines are controlled by a permeate back pressure regulator, and the permeate back pressure regulator and the permeate mass flow controller acts to maintain substantially equivalent sweep gas pressures on each planar membrane throughout a sampling cycle. Further, the flow through system where sweep gas is continuously applied and permeate continuously withdrawn greatly mitigates the generation of any concentration gradient within the individual membrane testing cells.

A digital controller positions the retentate multiport valve and the permeate multiport valve such that the retentate stream of an individual membrane testing cell and the permeate stream of the individual membrane testing cell are ported to the retentate sampling line and the permeate sampling line respectively, and at least the permeate stream is analyzed by a gas analysis means to evaluate the performance of a membrane retained within this individual membrane testing cell. The digital controller may cycle through all the membrane testing cells in the membrane testing system in this manner, such that the performance of all membranes retained in the membrane testing cells may be evaluated for the specific feed gas pressure, feed gas composition, sweep gas pressure, permeate gas composition, and other variables. In an embodiment, each membrane testing cell is further comprised of band heaters in thermal contact with its feed volume, allowing for temperature control of the membrane test cells.

In this manner, the membrane testing system provides the capability to test the individual performance of a plurality of planar membranes subjected to a feed gas on one side and a sweep gas on a second side by generating a continuous flow through system and relatively constant pressures and flow rates in the feed volume and sweep volume of each individual membrane testing cell. The membrane testing system mitigates the development of any concentration gradients in each membrane testing cell, and allows for maintenance of a constant differential pressure across each of the tested membranes during the duration of a testing cycle.

An individual membrane testing cell in the membrane testing system is illustrated at FIG. 1 and generally indicated at 101. As illustrated, membrane testing cell 101 is comprised of a feed volume 125 and a sweep volume 126 arranged on opposite sides of membrane holder 105. Membrane holder 105 is intended to hold a planar membrane such as planar membrane 106. In practice, a feed gas at a higher pressure flows through feed volume 125 and a sweep gas at a lower pressure flows through sweep volume 126, and planar membrane 106 fluidly isolates the two volumes. Planar membrane 106 is susceptible to the diffusion of a portion of the species from the feed volume to the sweep volume. The portion of those species which do not diffuse through planer membrane 106 exit feed volume 125, and sweep gas and the diffused species exit sweep volume 126. The flow of feed gas and the flow of sweep gas maintain the respective volumes at a substantially constant pressure, so that planar membrane 106 experiences a relatively constant differential pressure during the membrane testing.

At FIG. 1, feed volume 125 is a three-dimensional space enclosed by feed volume boundary 102, where feed volume boundary 102 is a two-dimensional geometric surface describing the geometric limits of the three-dimensional feed volume 125. Additionally, a longitudinal axis L passes through feed volume 125 as illustrated, such that some segment of the longitudinal axis L resides within feed volume boundary 102. The longitudinal axis L is a geometric line, and at FIG. 1, the longitudinal axis L passes through feed volume 125 and intersects feed volume boundary 102 at points 103 and 104. These points of intersection define a longitudinal distance $L_F$ of the feed volume, where the longitudinal distance $L_F$ is the portion of the longitudinal axis L within feed volume boundary 102 or, relative to FIG. 1, the segment of the longitudinal axis L between points 103 and 104.

Additionally, membrane holder 105 is in fluid communication with feed volume boundary 102 and feed volume 125. Further, membrane holder 105 is designed to restrain a planar membrane, such as planar membrane 106 comprised of a first planar membrane surface 107 and second planar membrane surface 108, where the first and second planar membrane surfaces are substantially parallel to one another. In an embodiment, membrane holder 105 restrains planar membrane 106 such that the longitudinal axis L intersects and is substantially perpendicular to both first planar membrane surface 107 and second planar membrane surface 108. Further, membrane holder 105 restrains planar membrane 106 such that first planar membrane surface 107 is in fluid communication with feed volume 125 and second membrane surface 108 is in fluid communication with sweep volume 126. Membrane holder 105 may be any arrangement known in the art and sufficient for holding a planar membrane within the relationships described.

Within this disclosure, a "planar membrane" means a material having a first surface and a second surface where the first surface and the second surface are substantially parallel surfaces, and where the material fits within a membrane holder which restrains the planer membrane in a stationary position when the planer membrane is subjected to unequal forces on the first surface and the second surfaces, such as a differential pressure. Here "substantially parallel" with respect to the first and second surface means the first and second surfaces are non-intersecting surfaces separated by some portion of the material comprising the planar membrane. Additionally, "substantially perpendicular" means that an angle measured from the longitudinal axis L to the first planar membrane surface 107 is between 80 degrees and 100 degrees, and that an angle measured from the longitudinal axis L to the second planar membrane surface 108 is between 80 degrees and 100 degrees.

Membrane testing cell 101 is further comprised of feed gas supply port 109 penetrating feed volume boundary 102 and in fluid communication with feed volume 125. Additionally, retentate conduit 110 intersects feed volume boundary 102 and is comprised of retentate suction 111 at a first end and retentate discharge 112 at a second end. An interior of retentate conduit 110 is in fluid communication with feed volume 125 through retentate suction 111. Additionally, membrane cell feed line 119 is in fluid communication with feed gas supply port 109, and membrane cell retentate line 120 is in fluid communication with retentate discharge 112.

In operation, membrane holder 105 and planar membrane 106 fluidly isolate feed volume 125 from sweep volume 126, and a feed gas enters feed volume 125 through membrane cell feed line 119 and feed gas supply port 109, pressurizing feed volume 125 with the feed gas. The feed gas pressurizing feed volume 125 contacts first planar membrane surface 107 at pressure and one or more species in the feed gas diffuse through planar membrane 106. The remaining feed gas constituents exit feed volume 125 through retentate suction 111 and are discharged as retentate through membrane cell retentate line 120.

Similarly at FIG. 1, sweep volume 126 is a three-dimensional space enclosed by sweep volume boundary 113, where sweep volume boundary 113 is a two-dimensional geometric surface describing the geometric limits of the three-dimensional sweep volume 126. Additionally, the longitudinal axis L passes through sweep volume 126, and some segment of the longitudinal axis L resides within sweep volume boundary 113. At FIG. 1, the longitudinal axis L passes through sweep volume 126 and intersects sweep volume boundary 113 at points 114 and 115, and a longitudinal distance $L_S$ of the sweep volume is the portion of the longitudinal axis L within sweep volume boundary 113 or, relative to FIG. 1, the segment of the longitudinal axis L between points 114 and 180. Membrane testing cell 101 is further comprised of sweep gas supply port 115 penetrating sweep volume boundary 113 and in fluid communication with sweep volume 126. Additionally, permeate conduit 116 intersects sweep volume boundary 113 and is comprised of permeate suction 117 at a first end and permeate discharge 118 at a second end. An interior of permeate conduit 116 is in fluid communication with sweep volume 126 through permeate suction 117. Additionally, membrane cell sweep line 121 is in fluid communication with sweep gas supply port 115, and membrane cell permeate line 122 is in fluid communication with permeate discharge 118.

In operation, a sweep gas enters sweep volume 126 through membrane cell sweep line 121 and sweep gas supply port 115, pressurizing sweep volume 126 with the sweep gas. As stated, membrane holder 105 and planar membrane 106 fluidly isolate feed volume 125 from sweep volume 126, producing a pressure drop across the membrane with typically a lower pressure in sweep volume 126 compared to feed volume 125. The sweep gas pressurizing sweep volume 126 entrains the species diffusing through planar membrane 106 and exiting through second planar membrane surface 108, and the sweep gas and diffused species exit sweep volume 126 through permeate suction 117 and are discharged as permeate through membrane cell permeate line 122. Through control of the feed gas flow rate, the sweep gas flow rate, the retentate flow rate, the permeate flow rate, the permeate back pressure, and the retentate back pressure, constant pressures and flow rates in flow volume 125 and sweep volume 126 can be maintained, and planar membrane 106 may be tested under a constant differential pressure condition. Additionally, membrane testing cell 101 may be further comprised of a means for controlling the temperature in feed volume 125, such as band heaters in thermal communication with feed volume 125, and a means for controlling the temperature in sweep volume 126, such as band heaters in thermal communication with sweep volume 126.

In the embodiment illustrated at FIG. 1, the longitudinal axis L additionally intersects retentate suction 111 and retentate discharge 112 of retentate conduit 110, and retentate conduit 110 surrounds some portion of the longitudinal distance $L_F$ of the feed volume, and similarly, the longitudinal axis L intersects permeate suction 117 and permeate discharge 118 of permeate conduit 116, and permeate conduit 116 surrounds some portion of the longitudinal distance $L_S$ of the sweep volume. In a further embodiment, feed volume 125 and sweep volume 126 are symmetric about longitudinal axis L. In another embodiment, retentate conduit 110 and permeate conduit 116 surround at least 80% of the longitudinal distance $L_F$ and the longitudinal distance $L_S$ respectively. In an additional embodiment, membrane testing cell 101 is further comprised of planar membrane 106 restrained by membrane holder 105, and retentate suction 111 is displaced from the first planar membrane surface by a first displacement, where the first displacement is less than 20% of the longitudinal distance $L_F$ of the feed volume and where the first displacement is measured in a direction parallel to the longitudinal axis L, and permeate suction 117 is displaced from the second planar membrane surface by a second displacement, where the second displacement is less than 20% of the longitudinal distance $L_S$ of the sweep volume and where the second displacement is measured in a direction parallel to the longitudinal axis L. In an embodiment, the first displacement is less than or equal to ten times the inside diameter of retentate conduit 110, and second displacement is less than or equal to ten times the inside diameter of permeate conduit 116. The symmetrical feed and sweep volumes combined with the relative proximity of the retentate and permeate suctions to the planar membrane has the advantage of generating a relatively uniform flow over the first and second planar membrane surfaces of the planar membrane as the gases are drawn from the respective volumes. In terms of membrane testing, this arrangement mitigates concentration gradients in the respective cells and allows substantially the entirety of the first planar membrane surface to be exposed to an essentially uniform flow of feed gas, and substantially the entirety of the second planar membrane surface to be swept by an essentially uniform flow of sweep gas. This is a significant advantage of the constant pressure membrane testing provided through the various flow arrangements of the disclosed apparatus.

Figure 2:
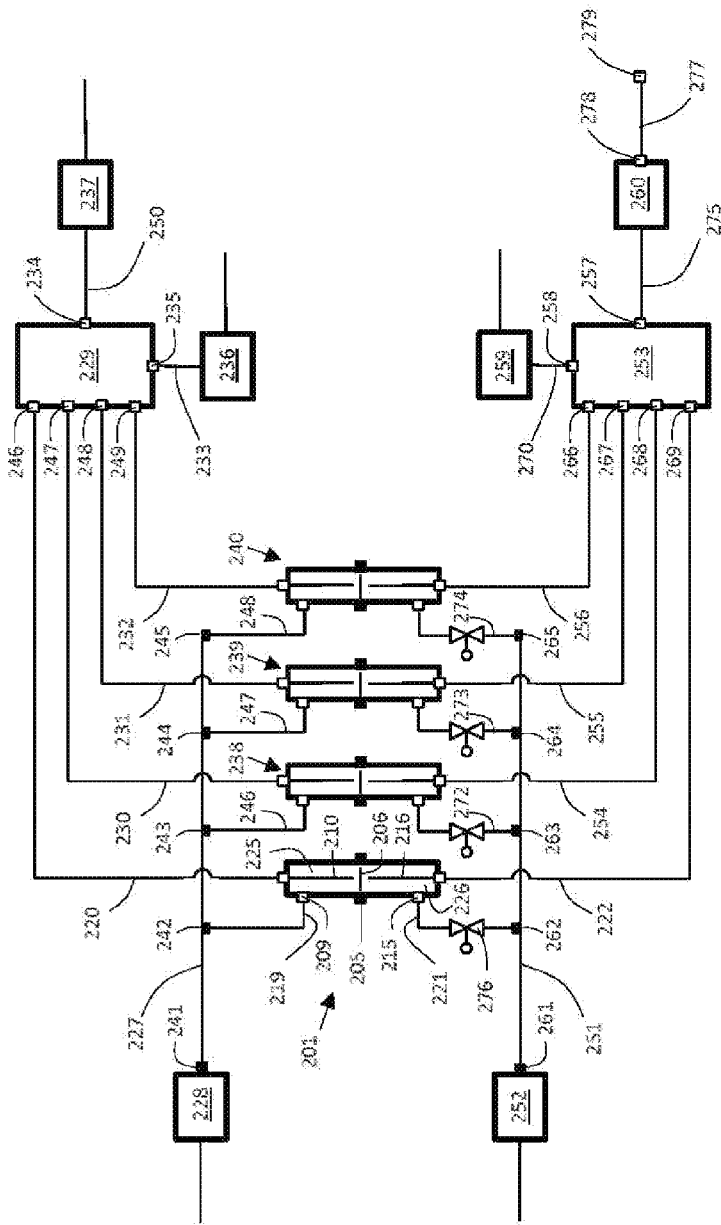
FIG. 2 illustrates a membrane testing system for a plurality of individual membrane testing cells.

The membrane testing system is further illustrated at FIG. 2. The membrane testing system is comprised of a plurality of membrane testing cells such as membrane testing cell 201. At FIG. 2, membrane testing cell 201 is comprised of feed volume 225, feed gas supply port 209, membrane cell feed line 219, retentate conduit 210, membrane cell retentate line 220, sweep volume 226, sweep gas supply port 215, membrane cell sweep line 221, permeate conduit 216, membrane cell permeate line 222, and membrane holder 205, where membrane holder 205 is depicted holding planar membrane 206. The respective components have the relationships as described for membrane testing cell 101. Additionally depicted are membrane testing cells 238, 239, and 240, all constructed similarly to membrane testing cell 201.

The membrane testing system at FIG. 2 is further comprised of a feed supply configuration, a retentate collection configuration, a sweep supply configuration, and a permeate collection configuration. The feed supply configuration is comprised of main feed line 227 having main feed inlet 241 and a plurality of main feed outlets 242, 243, 244, and 245. As illustrated, each main feed outlet is in fluid communication with one of the membrane cell feed lines 219, 246, 247, and 248. As a result, feed gas pressurizing main feed line 227 may act through each feed outlet, membrane cell feed line, and feed gas supply port to pressurize the feed volume of each membrane testing cell in the plurality of membrane testing cells 201, 238, 239, and 240. A feed mass flow controller 228 is in fluid communication with main feed inlet 241, providing for mass flow control of feed gas into main feed line 227.

The retentate collection configuration is comprised of a retentate multiport valve 229, retentate mass flow controller 237, and retentate back pressure regulator 236. Retentate multiport valve 229 is comprised of a plurality of ports serving as retentate inlet ports 246, 247, 248, and 249, retentate sampling port 234, and retentate venting port 235. Each retentate inlet port comprising retentate multiport valve 229 is in fluid communication with one membrane cell retentate line 220, 230, 231, and 232. Additionally, retentate mass flow controller 237 is in fluid communication with retentate sampling port 234 through conduit 250, and retentate back pressure regulator 236 is in fluid communication with retentate venting port 235 through conduit 233.

In operation, feed mass flow controller 228 is set to deliver a feed gas mass flow to main feed line 227, which pressurizes the feed volume of each membrane testing cell in the membrane testing system through the plurality of main feed outlets 242, 243, 244, and 245. The feed gas contacts each planar membrane in each membrane testing cell, and retentate from each cell is drawn through the individual membrane cell retentate lines. Retentate multiport valve 229 is positioned such that a single membrane cell retentate line is directed to sampling port 234 and retentate mass flow controller 237 while the remaining membrane cell retentate lines are directed to venting port 235 and retentate back pressure regulator 236. The retentate mass flow controller 237 is set to deliver some retentate mass flow less than the feed gas mass flow, and retentate back pressure regulator 236 is set to maintain a specific pressure felt through venting port 235 and the remaining membrane cell retentate lines. In this manner, sampling of the single membrane cell retentate line directed to sampling port 234 occurs while a constant pressure is maintained in the feed volumes of those cells not being sampled. Additionally, retentate mass flow controller 237 may be set to maintain a sampling flow rate generally equal to the feed gas mass flow delivered by feed mass flow controller 228 divided by the quantity of membrane testing cells in the membrane testing system, to assist in maintaining a substantially equivalent pressure in the sampled cell during sampling. In an embodiment, retentate mass flow controller 237 delivers a mass flow within 20% of the mass flow through feed mass flow controller 228 divided by the quantity of membrane testing cells.

The sweep supply configuration is comprised of main sweep line 251 having main sweep inlet 261 and a plurality of main sweep outlets 262, 263, 264, and 265. Each main sweep outlet is in fluid communication with one of the membrane cell sweep lines 221, 272, 273, and 274. Correspondingly, sweep gas pressurizing main sweep line 251 may act through each sweep outlet, membrane cell sweep line, and sweep gas supply port to pressurize the sweep volume of each membrane testing cell in the plurality of membrane testing cells 201, 238, 239, and 240. A sweep mass flow controller 252 is in fluid communication with main sweep inlet 261, providing for mass flow control of sweep gas into main sweep line 251.

The permeate collection configuration is comprised of a permeate multiport valve 253, permeate mass flow controller 260, and permeate back pressure regulator 259. Permeate multiport valve 253 is comprised of a plurality of ports serving as permeate inlet ports 266, 267, 268, and 269, permeate sampling port 257, and permeate venting port 258. Each permeate inlet port comprising permeate multiport valve 253 is in fluid communication with one membrane cell permeate line 222, 254, 255, and 256. Additionally, permeate mass flow controller 260 is in fluid communication with permeate sampling port 257 through conduit 275, and permeate back pressure regulator 259 is in fluid communication with permeate venting port 258 through conduit 270.

In operation, and concurrent with the delivery of feed gas to main feed line 227, sweep mass flow controller 252 is set to deliver a sweep gas mass flow to main sweep line 251, which pressurizes the sweep volume of each membrane testing cell in the membrane testing system through the plurality of main sweep outlets 262, 263, 264, and 265. The sweep gas contacts each planar membrane in each membrane testing cell, and permeate from each cell is drawn through the individual membrane cell permeate lines. Permeate multiport valve 253 is positioned such that a single membrane cell permeate line is directed to sampling port 257 and permeate mass flow controller 260 while the remaining membrane cell permeate lines are directed to venting port 258 and permeate back pressure regulator 259. The permeate mass flow controller 260 is set to deliver some permeate mass flow less than the sweep gas mass flow, and permeate back pressure regulator 259 is set to maintain a specific pressure felt through venting port 258 and the remaining membrane cell permeate lines. In this manner, sampling of the single membrane cell permeate line directed to sampling port 257 occurs while a constant pressure is maintained in the sweep volumes of those cells not being sampled. Additionally, permeate mass flow controller 260 may be set to maintain a sampling flow rate generally equal to the sweep gas mass flow delivered by sweep mass flow controller 252 divided by the quantity of membrane testing cells in the membrane testing system, to assist in maintaining a substantially equivalent pressure in the sampled cell during sampling. In an embodiment, permeate mass flow controller 260 delivers a mass flow within 20% of the mass flow through sweep mass flow controller 252 divided by the quantity of membrane testing cells.

Retentate multiport valve 229 is a switching valve comprised of a valve member which may be positioned such that fluid communication between one retentate inlet port and the retentate sampling port 234 may be established while maintaining fluid communication between the remainder of the retentate inlet ports and the retentate venting port 235. Similarly, permeate multiport valve 253 is a switching valve comprised of a valve member which may be positioned such that fluid communication between one permeate inlet port and the permeate sampling port 257 may be established while maintaining fluid communication between the remainder of the permeate inlet ports and the permeate venting port 258. Such switching valves are known in the art. In an embodiment where the membrane testing system of FIG. 2 is comprised of 16 individual membrane testing cells, retentate multiport valve 229 and permeate multiport valve 253 are serial interface, electrically actuated 16—way valves individually identified by product number EMTCSC16MWE, available from Valco Instruments Company, Inc., Houston, Tex.

Feed mass flow controller 228, sweep mass flow controller 252, retentate mass flow controller 237, and permeate mass flow controller 260 are mass flow controllers which measure and control a flow of gas or liquid over a particular range of flow rates. Such mass flow controllers are known in the art. The mass flow controller is typically comprised of an inlet port, an outlet port, a mass flow sensor and a proportional control valve, and typically the mass flow controller is fitted with a closed loop control system which compares an input value to a value from the mass flow sensor and adjusts the proportional valve accordingly. In an embodiment, feed mass flow controller 228 and sweep mass flow controller 252 are mass flow controllers individually identified by product number SLA5850S1BAB1C2A1, and retentate mass flow controller 237 and permeate mass flow controller 260 are mass flow controllers individually identified by product number SLA5850S1BAB1B2A1, available from Brooks Instrument, Hatfield, Pa.

Retentate back pressure regulator 236 and permeate back pressure regulator 259 are pressure regulating valves which modulate a flow of liquid or gas to maintain at a certain pressure. Such pressure regulating valves are known in the art. The pressure regulating valve is generally comprised of a restricting element and a loading element, where the restricting element is a typically a globe valve, butterfly valve, or poppet valve, and the loading element is typically a diaphragm, weight, spring, or piston which applies force to the restricting element. In an embodiment, retentate back pressure regulator 236 and permeate back pressure regulator 259 are pressure regulating valves individually identified by product number PC-100PSIG-D, OXC/5P available from Alicat Scientific, Inc., Tucson, Ariz.

In an embodiment, the membrane testing system is further comprised of a plurality of sweep isolation valves for isolating an individual membrane testing cell from main sweep line 251, such as isolation valve 276 between main sweep outlet 262 and sweep gas supply port 215 for the isolation of membrane testing cell 201. In an additional embodiment, the membrane testing system is further comprised of a plurality of feed isolation valves for isolating an individual membrane testing cell from main feed line 227, where each feed isolation valve in the plurality of feed isolation valves is positioned in the membrane cell feed line of the individual membrane testing cell between the feed gas supply port of the individual membrane testing cell and the main feed outlet in fluid communication with the membrane cell feed line of the individual membrane testing cell. The plurality of isolation valves serves to isolate a given membrane testing cell when indications of a planar membrane rupture during testing are detected. In an embodiment, the isolation valves are electrically actuated valves, and are placed in a shut position in response to rupture indications detected by a programmed controller in communication with a gas analysis means.

In an additional embodiment, the membrane testing system of FIG. 2 is comprised of permeate sampling conduit 277 having permeate sample inlet 278 in fluid communication with permeate sample outlet 279, where the permeate sample inlet 278 is in fluid communication with sampling port 257 of permeate multiport valve 253, and where permeate sample outlet 279 is in fluid communication with a gas analysis means, such as a mass spectrometer or other means known in the art for the determination of a gas composition.

The membrane testing system of FIG. 2 may be automated for the testing of a plurality of planar membranes by utilizing a digital controller, a retentate multiport valve having a serial interface, and a permeate multiport valve having a serial interface, where the digital controller is in data communication with the retentate multiport valve and the permeate multiport valve. The digital controller may be programmed to position permeate multiport valve 253 such that a cell permeate line for a given cell is in fluid communication with sampling port 257 while concurrently positioning retentate multiport valve 229 such that a cell retentate line for the given cell is in fluid communication with sampling port 234. For example, the digital controller may position the permeate multiport valve 253 and retentate multiport valve 229 such that cell permeate line 222 and cell retentate line 220 are in fluid communication with permeate mass flow controller 260 and retentate mass flow controller 237 respectively. Additionally, the digital controller may be programmed to conduct the operation cyclically so that, with respect to FIG. 2, the cell permeate line and cell retentate line of membrane testing cell 201 are in fluid communication with permeate mass flow controller 260 and retentate mass flow controller 237 respectively for a first period, then the cell permeate line and cell retentate line of membrane testing cell 238 are in fluid communication with permeate mass flow controller 260 and retentate mass flow controller 237 respectively for a second period, then cell permeate line and cell retentate line of membrane testing cell 239 are in fluid communication with permeate mass flow controller 260 and retentate mass flow controller 237 respectively for a third period, and so on, until the permeate multiport valve 253 and retentate multiport valve 229 have been positioned such that the cell permeate line and the cell retentate line of all membrane testing cells have similarly been in fluid communication with permeate mass flow controller 260 and retentate mass flow controller 237. Such an operation allows for essentially automated testing of a plurality of planar membranes when permeate sample outlet 279 is in fluid communication with a gas analysis means. The digital controller may further be in data communication with feed mass flow controller 228, sweep mass flow controller 252, permeate mass flow controller 260, and retentate mass flow controller 237. Digital controller programs which allow for such operations in measurement and control systems are known in the art. In an embodiment, the digital controller is a computer programmed with the software known as LABVIEW available from National Instruments Corporation, Austin, Tex.

An operation such as that described above allows for the testing of a plurality of planar membranes under similar feed gas composition, sweep gas composition, feed volume pressure, and sweep volume pressure using a minimum of necessary components. The capability is particularly useful when a large number of potential planar membranes may exist for a given set of conditions, and determination of the most suitable planar membrane must be determined through testing under the relevant conditions. The available automation of the system allows for testing over an extended time frame by cycling through and sampling the permeate composition exiting each individual membrane testing cell on a periodic basis as earlier described, while substantially constant pressures are maintained on the feed sides of all planar membranes and substantially constant pressures are maintained on the sweep sides of all planar membranes during the extended testing through the action of the feed mass flow controller 228, sweep mass flow controller 252, permeate multiport valve 253, permeate mass flow controller 260, permeate back pressure regulator 259, retentate multiport valve 229, retentate mass flow controller 237, and retentate back pressure regulator 236.

In an additional embodiment where the membrane testing system is comprised of a plurality of sweep isolation valves such as isolation valve 276, the digital controller is in data communication with each sweep isolation valve in the plurality of sweep isolation valves and in data communication with a means for detecting a planar membrane rupture in an affected cell, such as a ruptured membrane signal generated through a gas analysis means cyclically analyzing the permeate stream from the plurality of membrane testing cells. In this embodiment, when the planar membrane rupture in the affected cell is detected by the gas analysis means and a ruptured membrane signal is generated, the digital controller is programmed to shut the sweep isolation valve of the affected cell. In operation when sweep gas and feed gas are being supplied, when the sweep isolation valve of the affected cell is closed, this increases the sweep flow to the remaining cells. In order to overcome these consequences, in an embodiment where the digital controller is further in data communication with sweep mass flow controller 252, when the digital controller acts to shut the isolation valve of the affected cell, the digital controller is programmed to additionally communicate with sweep mass flow controller 252 to reduce the flow of sweep gas. In an embodiment, following the closure of a sweep isolation valve, the digital controller is programmed to communicate with sweep mass flow controller 252 and establish a setting where the sweep gas through sweep mass flow controller 252 is reduced by a factor substantially equivalent to $1/(M-N_S+1)$, where $N_S$ is equal to the quantity of sweep isolation valves closed and M is equal to the total quantity of membrane testing cells in the membrane testing system. Here, "substantially equivalent" means within 20% of the value of $1/(M-N_S+1)$.

In a further embodiment, where feed isolation valves in the membrane cell feed lines are not present or operated, in order to counter a decrease in feed flow to the remaining cells due to a membrane rupture, following the closure of a sweep isolation valve, the digital controller is programmed to communicate with feed mass flow controller 228 and establish a setting where the feed gas through feed mass flow controller 228 is increased by a factor substantially equivalent to $1/(M-N_S+1)$. In an additional embodiment where feed isolation valves in the membrane cell feed lines are present and operated, following the closure of a feed isolation valve, the digital controller is programmed to communicate with feed mass flow controller 228 and establish a setting where the feed gas through feed mass flow controller 228 is reduced by a factor substantially equivalent to $1/(M-N_F+1)$, where $N_F$ is equal to the quantity of feed isolation valves dosed. Here, "substantially equivalent" means within 20% of the value of $1/(M-N_F+1)$.

In an embodiment, a cell Mock comprises the plurality of membrane testing cells, and allows for placement and removal of planar membranes in a relatively easy manner. At FIG. 3, cell block 380 is comprised of separable blocks 381, 382, 383, and 384. Separable Nock 381 is a machined block forming a plurality of feed gas supply ports, such as feed gas supply port 309. Similarly, separable block 384 is a machined block forming a plurality of sweep gas supply ports, such as sweep gas supply port 315. Separable blocks 381, 382, 383, and 384 are maintained in contact and held in a constant alignment with respect to with each other by a fastening means, such as bolts 385 and 386 extending through separable blocks 381, 382, 383, and 384. At FIG. 3, cell block 380 is illustrated with respect to the coordinate axis shown, where the z-axis extends out of the page in a positive direction.

Figure 4:
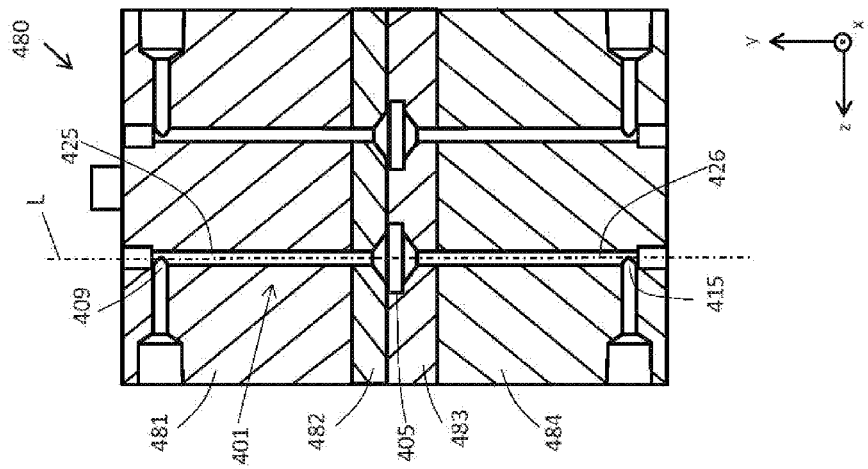
FIG. 4 illustrates a second view of a membrane testing cell block.
Figure 3:
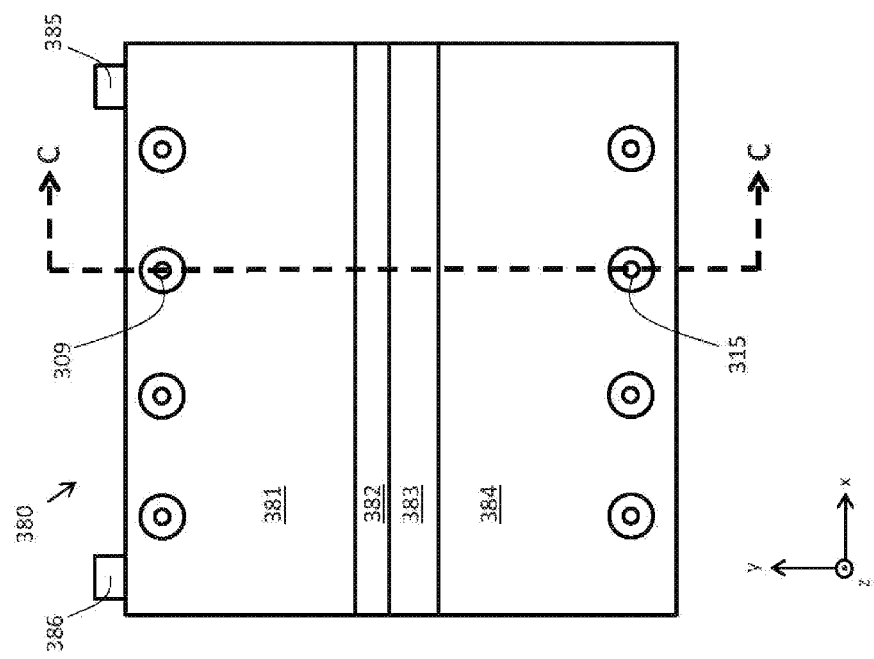
FIG. 3 illustrates a first view of a membrane testing cell block.

FIG. 4 illustrates the cell block rotated 90 degrees such that the x-axis extends out of the page in a positive direction, and further in a cut-away view based on the cutting plane C-C of FIG. 3. At FIG. 4, separable blocks 481 and 482 are comprised of a plurality of feed volumes such as feed volume 425 of the membrane testing cell generally indicated at 401, where feed volume 425 is a three-dimensional space enclosed by a feed volume boundary (not shown) and symmetrical about longitudinal axis L. Separable block 481 is additionally comprised of a plurality of feed gas supply ports, such as feed gas supply port 409 of membrane testing cell 401. Feed gas supply port 409 penetrates the feed volume boundary and is in fluid communication with feed volume 425.

Additionally, separable blocks 482 and 483 comprise membrane holder 405, which is in fluid communication with the feed volume boundary and feed volume 425. Membrane holder 405 is configured to restrain a planar membrane such that the longitudinal axis L intersects and is substantially perpendicular to both a first planar membrane surface and a second planar membrane surface, and restrains the planer membrane in a stationary position when the planar membrane is subjected to unequal forces on the first and the second planar membrane surfaces, such as a differential pressure. In practice, membrane holder 405 may additionally secure a sintered metal disk for support for a planar membrane, and may further support o-rings holding the planar membrane in place.

Similarly at FIG. 4, separable blocks 484 and 483 are comprised of a plurality of sweep volumes such as sweep volume 426 of membrane testing cell 401, where sweep volume 426 is a three-dimensional space enclosed by a sweep volume boundary (not shown) and symmetrical about longitudinal axis L. Separable block 484 is additionally comprised of a plurality of sweep gas supply ports, such as sweep gas supply port 415 of membrane testing cell 401. Sweep gas supply port 415 penetrates the sweep volume boundary and is in fluid communication with sweep volume 426. Membrane holder 405 is in fluid communication with the sweep volume boundary and sweep volume 426.

In an embodiment, feed volume 425 is a cylindrical volume generally having a diameter of about ¼ inch, feed gas supply port 409 is a generally circular area having a diameter of about ¼ inch, and the retentate conduit provides a generally circular retentate suction having a diameter of about $1/16^{th}$ inch. The generally cylindrical volume provides a longitudinal distance $L_F$ of feed volume 425 of greater than about 2 inches, and the retentate suction is displaced about ⅛ inch from a first surface of a planar membrane restrained by planar membrane holder 405. Additionally, feed gas supply port 409 is displaced from the retentate suction by a feed-retentate displacement equal to at least 80% of the longitudinal distance $L_F$, where the feed-retentate displacement has a direction parallel to the longitudinal axis L. Similarly, in this embodiment, sweep volume 426 is a cylindrical volume generally having a diameter of about ¼ inch, sweep gas supply port 415 is a generally circular area having a diameter of about ¼ inch, and the permeate conduit provides a generally circular permeate suction having a diameter of about $1/16^{th}$ inch. The generally cylindrical volume provides a longitudinal distance $L_s$ of sweep volume 426 of greater than about 2 inches, and the permeate suction is displaced about ⅛ inch from a second surface of the planar membrane restrained by planar membrane holder 405. Additionally, sweep gas supply port 415 is displaced from the permeate suction by a sweep-permeate displacement equal to at least 80% of the longitudinal distance $L_S$, where the sweep-permeate displacement has a direction parallel to the longitudinal axis L.

In an embodiment where the membrane testing system is further comprised of the gas analysis means and the digital controller, the membrane testing system may be utilized for testing a plurality of individual planar membranes using a particular feed gas and sweep gas by setting retentate back pressure regulator 236 to maintain a first pressure and setting permeate back pressure regulator 259 to maintain a second pressure, and additionally setting feed mass flow controller 228 to maintain a feed mass flow rate, sweep mass flow controller 252 to maintain a sweep mass flow rate, retentate mass flow controller 237 to maintain a retentate mass flow rate, and permeate mass flow controller 260 to maintain a permeate mass flow rate, where the retentate mass flow rate is less than the feed mass flow rate, and where the permeate mass flow rate is less than the sweep mass flow rate. The plurality of individual planar membranes may be tested using the particular feed and sweep gas by placing an individual membrane in the membrane holder of each membrane testing cell in the membrane testing system, such as membrane testing cell 201, 238, 239, and 240 of FIG. 2, then pressurizing main feed line 227 by placing feed mass flow controller 228 in fluid communication with a source of feed gas at a feed gas pressure, where the feed gas pressure is equal to or greater than the first pressure, thereby pressurizing each feed volume and placing a first side of each planar membrane in fluid communication with the feed gas. Similarly, main sweep line 251 is pressurized by placing sweep mass flow controller 252 in fluid communication with a source of sweep gas at a sweep gas pressure, where the sweep gas pressure is equal to or greater than the second pressure, thereby pressurizing each sweep volume placing a second side of each planar membrane in fluid communication with the sweep gas.

With each feed volume and sweep volume pressurized and opposite sides of each planar membrane in fluid communication with the feed and sweep gas respectively, and with feed mass flow controller 228 providing feed gas at a mass flow rate above that provided by retentate mass flow controller 237, retentate back pressure regulator 236 maintaining a pressure less than the source of feed gas, sweep mass flow controller 252 providing sweep gas at a mass flow rate above that provided by permeate mass flow controller 260, and permeate back pressure regulator 259 maintaining a pressure less than the source of sweep gas, the digital controller may position retentate multiport valve 229 and permeate multiport valve 253 such that the cell retentate outlet and the cell permeate outlet of a given membrane testing cell are in fluid communication with retentate sampling port 234 and permeate sampling port 257 respectively, while the cell retentate outlets and the cell permeate outlets of the remaining membrane testing cells are maintained in fluid communication with retentate back pressure regulator 236 and permeate back pressure regulator 253 respectively. This maintains the pressures in the feed and sweep volumes as well as mitigating any concentration gradients which might occur in the remaining cells while the given cell is being sampled. Additionally, in an embodiment, retentate mass flow controller 237 is set to provide a mass flow substantially equal to the mass flow of feed mass flow controller 228 divided by the total quantity of membrane testing cells, and permeate mass flow controller 260 is set to provide a mass flow substantially equal to the mass flow of sweep mass flow controller 252 divided by the total quantity of membrane testing cells, so that pressures in the feed and sweep volumes of the given membrane testing cell being sampled is similarly maintained.

Having positioned the retentate multiport valve 229 and permeate multiport valve 253 to provide a retentate stream from the given membrane testing cell, the permeate stream is analyzed by using the gas analysis means in fluid communication with permeate sampling port 257. Following the analysis, a second membrane testing cell is selected and the digital controller positions retentate multiport valve 229 and permeate multiport valve 253 such that the cell retentate outlet and the cell permeate outlet of the second membrane testing cell are in fluid communication with retentate sampling port 234 and permeate sampling port 257 respectively, while the cell retentate outlets and the cell permeate outlets of the remaining membrane testing cells are maintained in fluid communication with retentate back pressure regulator 236 and permeate back pressure regulator 253 respectively. Following analysis of the permeate stream of the second membrane testing cell by the gas analysis means, a third membrane testing cell is selected, and so on, until the permeate stream of all membrane testing cells have been analyzed. This operation may be repeated cyclically over some period of time, so that the permeate stream from each membrane in a membrane testing cell is analyzed multiple times over the period of time.

Thus the disclosure provides a membrane testing system providing the capability to test the individual performance of a plurality of planar membranes subjected to a feed gas on one side and a sweep gas on a second side, in a manner which mitigates the generation of concentration gradients on either side of a membrane, and allows maintaining a relatively constant differential pressure across the membrane during the testing. The membrane testing system provides a pressurized flow of a feed gas and a pressurized flow of a sweep gas to each membrane testing cell, and continuously withdraws retentate and permeate streams from each membrane testing cell. Relatively constant feed gas pressures are maintained by a feed mass controller in a main feed line operating in conjunction with a retentate multiport valve, a retentate mass flow controller, and a retentate back pressure regulator, while relatively constant sweep gas pressures are maintained by a sweep mass controller in a main sweep line operating in conjunction with a permeate multiport valve, a permeate mass flow controller, and a permeate back pressure regulator. A digital controller in data communication with the retentate multiport valve and the permeate multiport valve allows evaluation of all membranes retained in the membrane testing cells for the specific feed gas pressure, feed gas composition, sweep gas pressure, and other variables.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A membrane testing system comprising:
a plurality of membrane testing configurations, where each membrane testing configuration in the plurality of membrane testing configurations is comprised of,
a membrane testing cell, where the membrane testing cell is comprised of,
  a feed volume comprised of a feed volume boundary, where a longitudinal axis passes through the feed volume such that a segment of the longitudinal axis resides within the feed volume boundary, and where the feed volume defines a longitudinal distance of the feed volume, where the longitudinal distance of the feed volume is the segment of the longitudinal axis residing within the feed volume boundary,
  a membrane holder for restraining a planar membrane comprised of a first planar membrane surface and a second planar membrane surface, where the first planar membrane surface is substantially parallel to the second planar membrane surface, and where the membrane holder restrains the planar membrane such that the longitudinal axis intersects the first planar membrane surface and the second planar membrane surface, and where the membrane holder is in fluid communication with the feed volume boundary;
  a feed gas supply port penetrating the feed volume boundary and in fluid communication with the feed volume,
  a retentate conduit intersecting the feed volume boundary and comprised of a retentate suction at a first end of the retentate conduit and a retentate discharge at a second end of the retentate conduit, where the retentate suction is in fluid communication with the feed volume,
  a sweep volume comprised of a sweep volume boundary, where the sweep volume boundary is in fluid communication with the membrane holder, and where the longitudinal axis passes through the sweep volume such that a segment of the longitudinal axis resides within the sweep volume boundary, and where the sweep volume defines a longitudinal distance of the sweep volume, where the longitudinal distance of the sweep volume is the segment of the longitudinal axis residing within the sweep volume boundary;
  a sweep gas supply port penetrating the sweep volume boundary and in fluid communication with the sweep volume,
  a permeate conduit intersecting the sweep volume boundary and comprised of a permeate suction at a first end of the permeate conduit and a permeate discharge at a second end of the permeate conduit, where the permeate suction is in fluid communication with the sweep volume,
a membrane cell feed line comprised of a cell feed inlet and a cell feed outlet, where the cell feed inlet is in fluid communication with the cell feed outlet, and where the cell feed outlet is in fluid communication with the feed gas supply port of the membrane testing cell,
a membrane cell retentate line comprised of a cell retentate inlet and a cell retentate outlet, where the cell retentate inlet is in fluid communication with the cell retentate outlet, and where the cell retentate inlet is in fluid communication with the retentate discharge of the membrane testing cell,
a membrane cell sweep line comprised of a cell sweep inlet and a cell sweep outlet, where the cell sweep inlet is in fluid communication with the cell sweep outlet, and where the cell sweep outlet is in fluid communication with the sweep gas supply port of the membrane testing cell and,
a membrane cell permeate line comprised of a cell permeate inlet and a cell permeate outlet, where the cell permeate inlet is in fluid communication with the cell permeate outlet, and where the cell permeate inlet is in fluid communication with the permeate discharge of the membrane testing cell;
a feed supply configuration comprised of,
  a main feed line comprised of a main feed inlet and a plurality of main feed outlets, where each main feed outlet is in fluid communication with a single membrane cell feed line in the plurality of membrane testing configurations, and such that a singular membrane cell feed line in the plurality of membrane testing configurations is in fluid communication with one main feed outlet in the plurality of main feed outlets and, a feed mass flow controller in fluid communication with the main feed inlet;

a retentate collection configuration comprised of, a retentate multiport valve comprised of a plurality of retentate inlet ports, a retentate sampling port, and a retentate venting port, where each retentate inlet port in the plurality of retentate inlet ports is in fluid communication with a single cell retentate outlet in the plurality of membrane testing configurations, and such that a singular cell retentate outlet in the plurality of membrane testing configurations is in fluid communication with one retentate inlet port in the plurality of retentate inlet ports, a retentate mass flow controller in fluid communication with the retentate sampling port of the retentate multiport valve and, a retentate back pressure regulator in fluid communication with the retentate venting port of the retentate multiport valve; and a sweep supply configuration comprised of, a main sweep line comprised of a main sweep inlet and a plurality of main sweep outlets, where each main sweep outlet is in fluid communication with a single membrane cell sweep line in the plurality of membrane testing configurations, and such that a singular membrane cell sweep line in the plurality of membrane testing configurations is in fluid communication with one main sweep outlet in the plurality of main sweep outlets and, a sweep mass flow controller in fluid communication with the main sweep inlet;

a permeate collection configuration comprised of, a permeate multiport valve comprised of a plurality of permeate inlet ports, a permeate sampling port, and a permeate venting port, where each permeate inlet port in the plurality of permeate inlet ports is in fluid communication with a single cell permeate outlet in the plurality of membrane testing configurations, and such that a singular cell permeate outlet in the plurality of membrane testing configurations is in fluid communication with one permeate inlet port in the plurality of permeate inlet ports, a permeate mass flow controller in fluid communication with the permeate sampling port of the permeate multiport valve and, a permeate back pressure regulator in fluid communication with the permeate venting port of the permeate multiport valve.

2. The apparatus of claim 1 where each membrane cell sweep line in the plurality of membrane testing configurations is further comprised of a sweep isolation valve between the cell sweep inlet of the each membrane cell sweep line and the cell sweep outlet of the each membrane cell sweep line, such that the membrane testing system is further comprised of a plurality of sweep isolation valves.

3. The apparatus of claim 2 where each membrane cell feed line in the plurality of membrane testing configurations is further comprised of a feed isolation valve between the cell feed inlet of the each membrane cell sweep line and the cell feed outlet of the each membrane cell feed line, such that the membrane testing system is further comprised of a plurality of feed isolation valves.

4. The apparatus of claim 1 further comprised of a digital controller, where the digital controller is in data communication with at least an actuator for the retentate multiport valve and an actuator for the permeate multiport valve, and where the digital controller is programmed to position a valve member comprising the permeate multiport valve such that the cell permeate outlet of a specific membrane testing cell is in fluid communication with the permeate sampling port of the permeate multiport valve while concurrently positioning a valve member comprising the retentate multiport valve such that the cell retentate outlet of the specific membrane testing cell is in fluid communication with the retentate sampling port of the retentate multiport valve.

5. The apparatus of claim 4 where each membrane cell sweep line in the plurality of membrane testing configurations is further comprised of a sweep isolation valve between the cell sweep inlet of the each membrane cell sweep line and the cell sweep outlet of the each membrane cell sweep line, such that the membrane testing system is further comprised of a plurality of sweep isolation valves, and where the digital controller is in data communication with each sweep isolation valve in the plurality of sweep isolation valves, and where the digital controller is comprised of an input port for the reception of a ruptured membrane signal, and where the digital controller is programmed to shut the sweep isolation valve of the specific membrane testing cell when the ruptured membrane signal is received through the input port.

6. The apparatus of claim 5 where the digital controller is in data communication with the sweep mass flow controller and the feed mass flow controller, and where the digital controller is programmed to communicate with the sweep mass flow controller and the feed mass flow controller when the sweep isolation valve of the specific membrane testing cell is shut.

7. The apparatus of claim 6 where each membrane cell feed line in the plurality of membrane testing configurations is further comprised of a feed isolation valve between the cell feed inlet of the each membrane cell sweep line and the cell feed outlet of the each membrane cell feed line, such that the membrane testing system is further comprised of a plurality of feed isolation valves, and where the digital controller is in data communication with each feed isolation valve in the plurality of feed isolation valves, and where the digital controller is programmed to shut the feed isolation valve of the specific membrane testing cell when the ruptured membrane signal is received through the input port.

8. The apparatus of claim 1 where the retentate suction and the membrane holder are positioned such that the retentate suction is displaced from the first planar membrane surface by a first displacement measured parallel to the longitudinal axis, where the first displacement is less than or equal to ten times an inside diameter of the retentate suction, and where the permeate suction and the membrane holder are positioned such that the permeate suction is displaced from the second planar membrane surface by a second displacement measured parallel to the longitudinal axis, where the second displacement is less than or equal to ten times an inside diameter of the permeate suction.

9. A method of testing a plurality of membranes using the membrane testing system of claim 4 comprising:

placing an individual membrane in the membrane holder of each membrane testing configuration in the plurality of membrane testing configurations, thereby generating a plurality of loaded membrane testing configurations;

setting the retentate back pressure regulator to maintain a first pressure at the single retentate venting port of the retentate multiport valve;

setting the permeate back pressure regulator to maintain a second pressure at the single permeate venting port of the permeate multiport valve, where the second pressure is less than the first pressure;

pressurizing the main feed line by placing the feed mass flow controller in fluid communication with a source of feed gas at a feed gas pressure, where the feed gas pressure is equal to or greater than the first pressure, thereby pressurizing each feed volume comprising the plurality of loaded membrane testing configurations, and pressurizing the main sweep line by placing the sweep mass flow controller in fluid communication with a source of sweep gas at a sweep gas pressure, where the sweep gas pressure is equal to or greater than the second pressure, thereby pressurizing each sweep volume comprising the plurality of loaded membrane testing configurations;

setting the feed mass flow controller to maintain a feed mass flow rate, and setting the sweep mass flow controller to maintain a sweep mass flow rate; and setting the retentate mass flow controller to maintain a retentate mass flow rate, and setting the permeate mass flow controller to maintain a permeate mass flow rate, where the retentate mass flow rate is less than the feed mass flow rate, and where the permeate mass flow rate is less than the sweep mass flow rate;

utilizing the digital controller to position the valve member comprising the permeate multiport valve such that the cell permeate outlet of a first membrane testing configuration in the plurality of membrane testing configurations is in fluid communication with the permeate sampling port of the permeate multiport valve while concurrently positioning the valve member comprising the retentate multiport valve such that the cell retentate outlet of the first membrane testing configuration in the plurality of membrane testing configurations is in fluid communication with the retentate sampling port of the retentate multiport valve;

analyzing a permeate stream from the permeate sampling port of the permeate multiport valve using a gas analysis means, and selecting a second membrane testing configuration in the plurality of membrane testing configurations; and repeating the utilizing step and the analyzing step using the second membrane testing configuration in the plurality of membrane testing configurations as the first membrane testing configuration in the plurality of membrane testing configurations, and continuing the repeating until all membrane testing configurations in the plurality of membrane testing configurations have been utilized as the first membrane testing configuration in the plurality of membrane testing configurations at least a single time, thereby testing the plurality of membranes using the membrane testing system of claim 4.

10. The method of claim 9 further comprising:

determining a numerical quantity of membrane testing configurations, where the numerical quantity of membrane testing configurations is the number of membrane testing configurations in the plurality of membrane testing configurations;

setting the retentate mass flow controller to maintain the retentate mass flow rate where the retentate mass flow rate is within 20% of the feed mass flow rate divided by the numerical quantity of membrane testing configurations; and setting the permeate mass flow controller to maintain the permeate mass flow rate where the permeate mass flow rate is within 20% of the sweep mass flow rate divided by the numerical quantity of membrane testing configurations.

11. A method of testing a plurality of membranes using the membrane testing system of claim 6 comprising:

placing an individual membrane in the membrane holder of each membrane testing configuration in the plurality of membrane testing configurations, thereby generating a plurality of loaded membrane testing configurations;

setting the retentate back pressure regulator to maintain a first pressure at the single retentate venting port of the retentate multiport valve;

setting the permeate back pressure regulator to maintain a second pressure at the single permeate venting port of the permeate multiport valve, where the second pressure is less than the first pressure;

pressurizing the main feed line by placing the feed mass flow controller in fluid communication with a source of feed gas at a feed gas pressure, where the feed gas pressure is equal to or greater than the first pressure, thereby pressurizing each feed volume comprising the plurality of loaded membrane testing configurations, and pressurizing the main sweep line by placing the sweep mass flow controller in fluid communication with a source of sweep gas at a sweep gas pressure, where the sweep gas pressure is equal to or greater than the second pressure, thereby pressurizing each sweep volume comprising the plurality of loaded membrane testing configurations;

setting the feed mass flow controller to maintain a feed mass flow rate, and setting the sweep mass flow controller to maintain a sweep mass flow rate; and setting the retentate mass flow controller to maintain a retentate mass flow rate, and setting the permeate mass flow controller to maintain a permeate mass flow rate, where the retentate mass flow rate is less than the feed mass flow rate, and where the permeate mass flow rate is less than the sweep mass flow rate;

utilizing the digital controller to position the valve member comprising the permeate multiport valve such that the cell permeate outlet of a first membrane testing configuration in the plurality of membrane testing configurations is in fluid communication with the permeate sampling port of the permeate multiport valve while concurrently positioning the valve member comprising the retentate multiport valve such that the cell retentate outlet of the first membrane testing configuration in the plurality of membrane testing configurations is in fluid communication with the retentate sampling port of the retentate multiport valve;

analyzing a permeate stream from the permeate sampling port of the permeate multiport valve using a gas analysis means, and selecting a second membrane testing configuration in the plurality of membrane testing configurations; and repeating the utilizing step and the analyzing step using the second membrane testing configuration in the plurality of membrane testing configurations as the first membrane testing configuration in the plurality of membrane testing configurations, and continuing the repeating until all membrane testing configurations in the plurality of membrane testing configurations have been utilized as the first membrane testing configuration in the plurality of membrane testing configurations at least a single time, thereby testing the plurality of membranes using the membrane testing system determining a numerical quantity of membrane testing configurations, where the numerical quantity of membrane testing configurations is the number of membrane testing configurations in the plurality of membrane testing configurations;

setting the retentate mass flow controller to maintain the retentate mass flow rate where the retentate mass flow rate is within 20% of the feed mass flow rate divided by the numerical quantity of membrane testing configurations; and setting the permeate mass flow controller to maintain the permeate mass flow rate where the permeate mass flow rate is within 20% of the sweep mass flow rate divided by the numerical quantity of membrane testing configurations detecting an amount of a particular species in the permeate stream from the permeate sampling port of the permeate multiport valve using the gas analysis means;

shutting the sweep isolation valve of the specific membrane testing cell following the detecting the amount of the particular species, and determining a numerical quantity of shut sweep isolation valves, where the numerical quantity of shut sweep isolation valves is the number of sweep isolation valves in the shut position in the membrane testing system; and adjusting the sweep mass flow controller to reduce the sweep mass flow rate by a first factor substantially equivalent to $1/(M-N_S+1)$ and adjusting the feed mass flow controller to increase the feed mass flow rate by a second factor substantially equivalent to $1/(M-N_S+1)$, where M is equal to the numerical quantity of membrane testing configurations, and where $N_S$ is equal to the numerical quantity of shut sweep isolation valves.

12. The method of claim 11 further comprised of generating a ruptured membrane signal in response to detecting the amount of the particular species, receiving the ruptured membrane signal through the input port of the digital controller, and communicating a shut signal from the digital controller to the sweep isolation valve of the specific membrane testing cell, where the shut signal causes the sweep isolation valve of the specific membrane testing cell to shut, thereby shutting the sweep isolation valve of the specific membrane testing cell, and further comprised of communicating a reduce sweep flow signal from the digital controller to the sweep mass flow controller, where the reduce sweep flow signal causes the sweep mass flow controller to reduce the sweep mass flow rate by the first factor, thereby adjusting the sweep mass flow controller, and further comprised of communicating an increase feed flow signal from the digital controller to the feed mass flow controller, where the increase feed flow signal causes the feed mass flow controller to increase the feed mass flow rate by the second factor, thereby adjusting the feed mass flow controller.

13. A method of testing a plurality of membranes using the membrane testing system of claim 7 comprising:

placing an individual membrane in the membrane holder of each membrane testing configuration in the plurality of membrane testing configurations, thereby generating a plurality of loaded membrane testing configurations;

setting the retentate back pressure regulator to maintain a first pressure at the single retentate venting port of the retentate multiport valve;

setting the permeate back pressure regulator to maintain a second pressure at the single permeate venting port of the permeate multiport valve, where the second pressure is less than the first pressure;

pressurizing the main feed line by placing the feed mass flow controller in fluid communication with a source of feed gas at a feed gas pressure, where the feed gas pressure is equal to or greater than the first pressure, thereby pressurizing each feed volume comprising the plurality of loaded membrane testing configurations, and pressurizing the main sweep line by placing the sweep mass flow controller in fluid communication with a source of sweep gas at a sweep gas pressure, where the sweep gas pressure is equal to or greater than the second pressure, thereby pressurizing each sweep volume comprising the plurality of loaded membrane testing configurations;

setting the feed mass flow controller to maintain a feed mass flow rate, and setting the sweep mass flow controller to maintain a sweep mass flow rate; and setting the retentate mass flow controller to maintain a retentate mass flow rate, and setting the permeate mass flow controller to maintain a permeate mass flow rate, where the retentate mass flow rate is less than the feed mass flow rate, and where the permeate mass flow rate is less than the sweep mass flow rate;

utilizing the digital controller to position the valve member comprising the permeate multi port valve such that the cell permeate outlet of a first membrane testing configuration in the plurality of membrane testing configurations is in fluid communication with the permeate sampling port of the permeate multi port valve while concurrently positioning the valve member comprising the retentate multiport valve such that the cell retentate outlet of the first membrane testing configuration in the plurality of membrane testing configurations is in fluid communication with the retentate sampling port of the retentate multi port valve;

analyzing a permeate stream from the permeate sampling port of the permeate multiport valve using a gas analysis means, and selecting a second membrane testing configuration in the plurality of membrane testing configurations; and repeating the utilizing step and the analyzing step using the second membrane testing configuration in the plurality of membrane testing configurations as the first membrane testing configuration in the plurality of membrane testing configurations, and continuing the repeating until all membrane testing configurations in the plurality of membrane testing configurations have been utilized as the first membrane testing configuration in the plurality of membrane testing configurations at least a single time, thereby testing the plurality of membranes using the membrane testing system determining a numerical quantity of membrane testing configurations, where the numerical quantity of membrane testing configurations is the number of membrane testing configurations in the plurality of membrane testing configurations;

setting the retentate mass flow controller to maintain the retentate mass flow rate where the retentate mass flow rate is within 20% of the feed mass flow rate divided by the numerical quantity of membrane testing configurations; and setting the permeate mass flow controller to maintain the permeate mass flow rate where the permeate mass flow rate is within 20% of the sweep mass flow rate divided by the numerical quantity of membrane testing configurations detecting an amount of a particular species in the permeate stream from the permeate sampling port of the permeate multiport valve using the gas analysis means;

shutting the sweep isolation valve of the specific membrane testing cell following the detecting the amount of the particular species shutting the feed isolation valve of the specific membrane testing cell following the detecting the amount of the particular species, and determining a numerical quantity of shut feed isolation valves, where the numerical quantity of shut feed isolation valves is the number of feed isolation valves in the shut position in the membrane testing system; and adjusting the sweep mass flow controller to reduce the sweep mass flow rate by a first factor substantially equivalent to $1/(M-N_S+1)$ and adjusting the feed mass flow controller to reduce the feed mass flow rate by a third factor substantially equivalent to $1/(M-N_F+1)$, where M is equal to the numerical quantity of membrane testing configurations, and where $N_S$ is equal to the numerical quantity of shut sweep isolation valves, and where $N_F$ is equal to the numerical quantity of shut feed isolation valves.

14. The method of claim 13 further comprised of generating a ruptured membrane signal in response to detecting the amount of the particular species, receiving the ruptured membrane signal through the input port of the digital controller, and communicating a first shut signal from the digital controller to the sweep isolation valve of the specific membrane testing cell, where the first shut signal causes the sweep isolation valve of the specific membrane testing cell to shut, thereby shutting the sweep isolation valve of the specific membrane testing cell, and further comprising communicating a second shut signal from the digital controller to the feed isolation valve of the specific membrane testing cell, where the second shut signal causes the feed isolation valve of the specific membrane testing cell to shut, thereby shutting the feed isolation valve of the specific membrane testing cell, and further comprising communicating a reduce sweep flow signal from the digital controller to the sweep mass flow controller, where the reduce sweep flow signal causes the sweep mass flow controller to reduce the sweep mass flow rate by the first factor, thereby adjusting the sweep mass flow controller, and further comprising communicating a reduce feed flow signal from the digital controller to the feed mass flow controller, where the reduce feed flow signal causes the feed mass flow controller to reduce the feed mass flow rate by the third factor, thereby adjusting the feed mass flow controller.

15. A membrane testing system comprising:

a plurality of membrane testing configurations where each membrane testing configuration in the plurality of membrane testing configurations is comprised of, a membrane testing cell, where the membrane testing cell is comprised of, a feed volume comprised of a feed volume boundary, where a longitudinal axis passes through the feed volume such that a segment of the longitudinal axis resides within the feed volume boundary, and where the feed volume defines a longitudinal distance of the feed volume, where the longitudinal distance of the feed volume is the segment of the longitudinal axis residing within the feed volume boundary, a membrane holder for restraining a planar membrane comprised of a first planar membrane surface and a second planar membrane surface, where the first planar membrane surface is substantially parallel to the second planar membrane surface, and where the membrane holder restrains the planar membrane such that the longitudinal axis intersects the first planar membrane surface and the second planar membrane surface, and where the membrane holder is in fluid communication with the feed volume boundary;

a feed gas supply port penetrating the feed volume boundary and in fluid communication with the feed volume, a retentate conduit intersecting the feed volume boundary and comprised of a retentate suction at a first end of the retentate conduit and a retentate discharge at a second end of the retentate conduit, where the retentate suction is in fluid communication with the feed volume, a sweep volume comprised of a sweep volume boundary, where the sweep volume boundary is in fluid communication with the membrane holder, and where the longitudinal axis passes through the sweep volume such that a segment of the longitudinal axis resides within the sweep volume boundary, and where the sweep volume defines a longitudinal distance of the sweep volume, where the longitudinal distance of the sweep volume is the segment of the longitudinal axis residing within the sweep volume boundary;

a sweep gas supply port penetrating the sweep volume boundary and in fluid communication with the sweep volume, a permeate conduit intersecting the sweep volume boundary and comprised of a permeate suction at a first end of the permeate conduit and a permeate discharge at a second end of the permeate conduit, where the permeate suction is in fluid communication with the sweep volume, a membrane cell feed line comprised of a cell feed inlet and a cell feed outlet, where the cell feed inlet is in fluid communication with the cell feed outlet, and where the cell feed outlet is in fluid communication with the feed gas supply port of the membrane testing cell, a membrane cell retentate line comprised of a cell retentate inlet and a cell retentate outlet, where the cell retentate inlet is in fluid communication with the cell retentate outlet, and where the cell retentate inlet is in fluid communication with the retentate discharge of the membrane testing cell, a membrane cell sweep line comprised of a cell sweep inlet and a cell sweep outlet and comprised of a sweep isolation valve between the cell sweep inlet and the cell sweep outlet, and where the cell sweep outlet is in fluid communication with the sweep gas supply port of the membrane testing cell and, a membrane cell permeate line comprised of a cell permeate inlet and a cell permeate outlet, where the cell permeate inlet is in fluid communication with the cell permeate outlet, and where the cell permeate inlet is in fluid communication with the permeate discharge of the membrane testing cell;

a feed supply configuration comprised of, a main feed line comprised of a main feed inlet and a plurality of main feed outlets, where each main feed outlet is in fluid communication with a single membrane cell feed line in the plurality of membrane testing configurations, and such that a singular membrane cell feed line in the plurality of membrane testing configurations is in fluid communication with one main feed outlet in the plurality of main feed outlets and, a feed mass flow controller in fluid communication with the main feed inlet;
a retentate collection configuration comprised of,
a retentate multiport valve comprised of a plurality of retentate inlet ports, a single retentate sampling port, and a single retentate venting port, where each retentate inlet port in the plurality of retentate inlet ports is in fluid communication with a single cell retentate outlet in the plurality of membrane testing configurations, and such that a singular cell retentate outlet in the plurality of membrane testing configurations is in fluid communication with one retentate inlet port in the plurality of retentate inlet ports,
a retentate mass flow controller in fluid communication with the single retentate sampling port of the retentate multiport valve and,
a retentate back pressure regulator in fluid communication with the single retentate venting port of the retentate multiport valve;
a sweep supply configuration comprised of,
a main sweep line comprised of a main sweep inlet and a plurality of main sweep outlets, where each main sweep outlet is in fluid communication with a single membrane cell sweep line in the plurality of membrane testing configurations, and such that a singular membrane cell sweep line in the plurality of membrane testing configurations is in fluid communication with one main sweep outlet in the plurality of main sweep outlets and,
a sweep mass flow controller in fluid communication with the main sweep inlet;
a permeate collection configuration comprised of,
a permeate multiport valve comprised of a plurality of permeate inlet ports, a single permeate sampling port, and a single permeate venting port, where each permeate inlet port in the plurality of permeate inlet ports is in fluid communication with a single cell permeate outlet in the plurality of membrane testing configurations, and such that a singular cell permeate outlet in the plurality of membrane testing configurations is in fluid communication with one permeate inlet port in the plurality of permeate inlet ports,
a permeate mass flow controller in fluid communication with the single permeate sampling port of the permeate multiport valve and,
a permeate back pressure regulator in fluid communication with the single permeate venting port of the permeate multiport valve; and
a digital controller, where the digital controller is in data communication with an actuator for the retentate multiport valve and an actuator for the permeate multiport valve, and where the digital controller is programmed to position a valve member comprising the permeate multiport valve such that the cell permeate outlet of a specific membrane testing cell is in fluid communication with the single permeate sampling port of the permeate multiport valve while concurrently positioning a valve member comprising the retentate multiport valve such that the cell retentate outlet of the specific membrane testing cell is in fluid communication with the single retentate sampling port of the retentate multiport valve, and where the digital controller is in data communication with the feed mass flow controller and the sweep mass flow controller, and where the digital controller is in data communication with each sweep isolation valve, where the digital controller is comprised of an input port for the reception of a ruptured membrane signal, where the digital controller is programmed to shut the sweep isolation valve of the specific membrane testing cell when the ruptured membrane signal is received through the input port.

16. A method of testing a plurality of membranes using the membrane testing system of claim 15 comprising:
determining a numerical quantity of membrane testing configurations, where the numerical quantity of membrane testing configurations is the number of membrane testing configurations in the plurality of membrane testing configurations;
placing an individual membrane in the membrane holder of each membrane testing configuration in the plurality of membrane testing configurations, thereby generating a plurality of loaded membrane testing configurations;
setting the retentate back pressure regulator to maintain a first pressure at the single retentate venting port of the retentate multiport valve;
setting the permeate back pressure regulator to maintain a second pressure at the single permeate venting port of the permeate multiport valve, where the second pressure is less than the first pressure;
pressurizing the main feed line by placing the feed mass flow controller in fluid communication with a source of feed gas at a feed gas pressure, where the feed gas pressure is equal to or greater than the first pressure, thereby pressurizing each feed volume comprising the plurality of loaded membrane testing configurations, and pressurizing the main sweep line by placing the sweep mass flow controller in fluid communication with a source of sweep gas at a sweep gas pressure, where the sweep gas pressure is equal to or greater than the second pressure, thereby pressurizing each sweep volume comprising the plurality of loaded membrane testing configurations;
setting the feed mass flow controller to maintain a feed mass flow rate, and setting the sweep mass flow controller to maintain a sweep mass flow rate; and setting the retentate mass flow controller to maintain a retentate mass flow rate, and setting the permeate mass flow controller to maintain a permeate mass flow rate, where the retentate mass flow rate is less than the feed mass flow rate, and where the permeate mass flow rate is less than the sweep mass flow rate, and where the retentate mass flow rate is within 20% of the feed mass flow rate divided by the numerical quantity of membrane testing configurations, and where the permeate mass flow rate is within 20% of the sweep mass flow rate divided by the numerical quantity of membrane testing configurations;
utilizing the digital controller to position the valve member comprising the permeate multiport valve such that the cell permeate outlet of a first membrane testing configuration in the plurality of membrane testing configurations is in fluid communication with the permeate sampling port of the permeate multiport valve while concurrently positioning the valve member comprising the retentate multiport valve such that the cell retentate outlet of the first membrane testing configuration in the plurality of membrane testing configurations is in fluid communication with the retentate sampling port of the retentate multiport valve;
analyzing a permeate stream from the permeate sampling port of the permeate multiport valve using a gas analysis means;
evaluating the permeate stream for an amount of a particular species in the permeate stream using the gas analysis means, and if the amount of the particular species in the permeate stream is detected, shutting the sweep isolation valve of the specific membrane testing cell and determining a numerical quantity of shut sweep isolation valves, where the numerical quantity of shut sweep isolation valves is the number of sweep isolation valves in the shut position in the membrane testing system, and adjusting the sweep mass flow controller to reduce the sweep mass flow rate by a first factor substantially equivalent to $1/(M-N_S+1)$ and adjusting the feed mass flow controller to increase the feed mass flow rate by a second factor substantially equivalent to $1/(M-N_S+1)$, where M is equal to the numerical quantity of membrane testing configurations, and where $N_S$ is equal to the numerical quantity of shut sweep isolation valves;

selecting a second membrane testing configuration in the plurality of membrane testing configurations;

repeating the utilizing step, the analyzing step, the evaluating step, and the selecting step using the second membrane testing configuration in the plurality of membrane testing configurations as the first membrane testing configuration in the plurality of membrane testing configurations, and continuing the repeating until all membrane testing configurations in the plurality of membrane testing configurations have been utilized as the first membrane testing configuration in the plurality of membrane testing configurations at least a single time, thereby testing the plurality of membranes using the membrane testing system of claim 15.

17. The method of claim 16 further comprised of generating a ruptured membrane signal in response to detecting the amount of the particular species, receiving the ruptured membrane signal through the input port of the digital controller, and communicating a shut signal from the digital controller to the sweep isolation valve of the specific membrane testing cell, where the shut signal causes the sweep isolation valve of the specific membrane testing cell to shut, thereby shutting the sweep isolation valve of the specific membrane testing cell, and further comprised of communicating a reduce sweep flow signal from the digital controller to the sweep mass flow controller, where the reduce sweep flow signal causes the sweep mass flow controller to reduce the sweep mass flow rate by the first factor, thereby adjusting the sweep mass flow controller, and further comprised of communicating an increase feed flow signal from the digital controller to the feed mass flow controller, where the increase feed flow signal causes the feed mass flow controller to increase the feed mass flow rate by the second factor, thereby adjusting the feed mass flow controller.

18. The apparatus of claim 15 where each membrane cell feed line in the plurality of membrane testing configurations is further comprised of a feed isolation valve between the cell feed inlet of the each membrane cell sweep line and the cell feed outlet of the each membrane cell feed line, such that the membrane testing system is further comprised of a plurality of feed isolation valves, and where the digital controller is in data communication with each feed isolation valve in the plurality of feed isolation valves, and where the digital controller is programmed to shut the feed isolation valve of the specific membrane testing cell when the ruptured membrane signal is received through the input port.

19. A method of testing a plurality of membranes using the membrane testing system of claim 18 comprising:

determining a numerical quantity of membrane testing configurations, where the numerical quantity of membrane testing configurations is the number of membrane testing configurations in the plurality of membrane testing configurations;

placing an individual membrane in the membrane holder of each membrane testing configuration in the plurality of membrane testing configurations, thereby generating a plurality of loaded membrane testing configurations;

setting the retentate back pressure regulator to maintain a first pressure at the single retentate venting port of the retentate multiport valve;

setting the permeate back pressure regulator to maintain a second pressure at the single permeate venting port of the permeate multiport valve, where the second pressure is less than the first pressure;

pressurizing the main feed line by placing the feed mass flow controller in fluid communication with a source of feed gas at a feed gas pressure, where the feed gas pressure is equal to or greater than the first pressure, thereby pressurizing each feed volume comprising the plurality of loaded membrane testing configurations, and pressurizing the main sweep line by placing the sweep mass flow controller in fluid communication with a source of sweep gas at a sweep gas pressure, where the sweep gas pressure is equal to or greater than the second pressure, thereby pressurizing each sweep volume comprising the plurality of loaded membrane testing configurations;

setting the feed mass flow controller to maintain a feed mass flow rate, and setting the sweep mass flow controller to maintain a sweep mass flow rate; and setting the retentate mass flow controller to maintain a retentate mass flow rate, and setting the permeate mass flow controller to maintain a permeate mass flow rate, where the retentate mass flow rate is less than the feed mass flow rate, and where the permeate mass flow rate is less than the sweep mass flow rate, and where the retentate mass flow rate is within 20% of the feed mass flow rate divided by the numerical quantity of membrane testing configurations, and where the permeate mass flow rate is within 20% of the sweep mass flow rate divided by the numerical quantity of membrane testing configurations;

utilizing the digital controller to position the valve member comprising the permeate multiport valve such that the cell permeate outlet of a first membrane testing configuration in the plurality of membrane testing configurations is in fluid communication with the permeate sampling port of the permeate multiport valve while concurrently positioning the valve member comprising the retentate multiport valve such that the cell retentate outlet of the first membrane testing configuration in the plurality of membrane testing configurations is in fluid communication with the retentate sampling port of the retentate multiport valve;

analyzing a permeate stream from the permeate sampling port of the permeate multiport valve using a gas analysis means;

evaluating the permeate stream for an amount of a particular species in the permeate stream using the gas analysis means, and if the amount of the particular species in the permeate stream is detected, shutting the sweep isolation valve of the specific membrane testing cell and determining a numerical quantity of shut sweep isolation valves, where the numerical quantity of shut sweep isolation valves is the number of sweep isolation valves in the shut position in the membrane testing system, and shutting the feed isolation valve of the specific membrane testing cell and determining a numerical quantity of shut feed isolation valves, where the numerical quantity of shut feed isolation valves is the number of feed isolation valves in the shut position in the membrane testing system, and adjusting the sweep mass flow controller to reduce the sweep mass flow rate by a first factor substantially equivalent to $1/(M-N_S+1)$, and adjusting the feed mass flow controller to reduce the feed mass flow rate by a second factor substantially equivalent to $1/(M-N_F+1)$, where M is equal to the numerical quantity of membrane testing configurations, and where $N_S$ is equal to the numerical quantity of shut sweep isolation valves, and where $N_F$ is equal to the numerical quantity of shut feed isolation valves;

selecting a second membrane testing configuration in the plurality of membrane testing configurations;

repeating the utilizing step, the analyzing step, the evaluating step, and the selecting step using the second membrane testing configuration in the plurality of membrane testing configurations as the first membrane testing configuration in the plurality of membrane testing configurations, and continuing the repeating until all membrane testing configurations in the plurality of membrane testing configurations have been utilized as the first membrane testing configuration in the plurality of membrane testing configurations at least a single time, thereby testing the plurality of membranes using the membrane testing system of claim 15.

20. The method of claim 19 further comprised of generating a ruptured membrane signal in response to detecting the amount of the particular species, receiving the ruptured membrane signal through the input port of the digital controller, and communicating a first shut signal from the digital controller to the sweep isolation valve of the specific membrane testing cell, where the first shut signal causes the sweep isolation valve of the specific membrane testing cell to shut, thereby shutting the sweep isolation valve of the specific membrane testing cell, and further comprising communicating a second shut signal from the digital controller to the feed isolation valve of the specific membrane testing cell, where the second shut signal causes the feed isolation valve of the specific membrane testing cell to shut, thereby shutting the feed isolation valve of the specific membrane testing cell, and further comprising communicating a reduce sweep flow signal from the digital controller to the sweep mass flow controller, where the reduce sweep flow signal causes the sweep mass flow controller to reduce the sweep mass flow rate by the first factor, thereby adjusting the sweep mass flow controller, and further comprising communicating a reduce feed flow signal from the digital controller to the feed mass flow controller, where the reduce feed flow signal causes the feed mass flow controller to reduce the feed mass flow rate by the second factor, thereby adjusting the feed mass flow controller.

\* \* \* \* \*